United States Patent [19]

Nitta et al.

[11] Patent Number: 4,602,009

[45] Date of Patent: Jul. 22, 1986

[54] CORTICOID DERIVATIVES AND PROCESS FOR PRODUCTION THEREOF

[75] Inventors: Issei Nitta, Machida; Akira Maruyama, Yokohama; Kenichiro Nakao; Motoyoshi Miyake, both of Tokyo; Hiroaki Ueno, Yokohama, all of Japan

[73] Assignee: Mitsubishi Chemical Industries, Ltd., Tokyo, Japan

[21] Appl. No.: 645,100

[22] Filed: Aug. 28, 1984

[30] Foreign Application Priority Data

Jun. 12, 1984 [JP] Japan .................................. 59-120439

[51] Int. Cl.$^4$ ............................................. A61K 31/56

[52] U.S. Cl. ............................... 514/179; 260/397.45; 260/239.55 D; 514/180

[58] Field of Search ................... 260/397.45; 514/179, 514/180

Primary Examiner—Elbert L. Roberts
Attorney, Agent, or Firm—Oblon, Fisher, Spivak, McClelland & Maier

[57] ABSTRACT

Novel corticoid 17α-alkoxycarbonyl carboxylate derivatives are disclosed. These derivatives have strong topical anti-inflammatory activity and extremely weak systemic adverse reactions and are useful for the treatment of acute and chronic eczema, eczema seborrhoicorum, contact dermatitis, atopic dermatitis, asthma, etc.

14 Claims, No Drawings

CORTICOID DERIVATIVES AND PROCESS FOR PRODUCTION THEREOF

BACKGROUND OF THE INVENTION

This invention relates to novel corticoid derivatives. Corticoid derivatives have anti-inflammatory activity and are useful as pharmaceuticals. As corticoid derivatives, 6-oxygenated corticoids are disclosed in Japanese Unexamined Patent Publication No. 73765/79 and corticoid 17α-carbonates are disclosed in Japanese Unexamined Patent Publication No. 36248/79. However, novel derivatives that have more efficacy as pharmaceuticals are always in demand.

The present inventors have synthesized corticoid 17α-alkoxycarbonyl carboxylate derivatives and found that they have strong topical anti-inflammatory activity and extremely weak systemic adverse reactions and that they are useful for the treatment of acute and chronic eczema, eczema seborrhoicorum, contact dermatitis, atopic dermatitis, asthma, etc. Thus, the present invention has been completed.

SUMMARY OF THE INVENTION

Corticoid 17α-alkoxycarbonyl carboxylate derivatives of the present invention are represented by the following general formula (I):

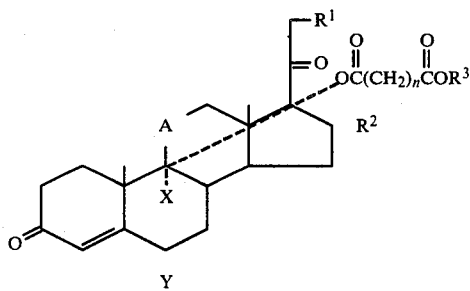

[wherein A is a group

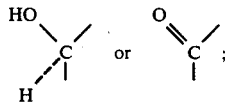

X is a hydrogen atom or halogen atom; Y is a hydrogen atom, oxo group, or halogen atom, hydroxy group or alkyl group having 1 to 10 carbon atoms at α- or β-position; n is an integer of 2 to 5; $R^1$ is a hydroxy group, halogen atom, a group represented by the following formula (II):

$$-OSO_2R^4 \qquad (II)$$

(wherein $R^4$ is an alkyl group or halogenated alkyl group having 1 to 10 carbon atoms) or a group represented by the following formula (III):

$$-OCOR^5 \qquad (III)$$

(wherein $R^5$ is an alkyl group or halogenated alkyl group having 1 to 10 carbon atoms); $R^2$ is a hydrogen atom or alkyl group having 1 to 10 carbon atoms at the α- or β-position; $R^3$ is an alkyl group having 1 to 10 carbon atoms; and the bond between $C_1$ and $C_2$ is a single bond or double bond].

DETAILED DESCRIPTION OF THE INVENTION

In explaining the present invention in detail, corticoid 17α-alkoxycarbonyl carboxylate derivatives of the present invention are represented by the above formula (I).

In the above formula, X is a hydrogen atom or halogen atom selected from fluorine, chlorine, bromine and iodine and, particularly, fluorine and chlorine are preferred. Y is a hydrogen atom, oxo group, or halogen atom, hydroxy group or alkyl group having 1 to 10 carbon atoms such as methyl, ethyl, propyl, butyl groups, etc. at the α- or β-position and particularly hydrogen atom and oxo group are preferred.

$R^1$ is a hydroxy group, halogen atom selected from fluorine, chlorine, bromine and iodine, a group represented by the following formula (III):

$$-OSO_2R^4 \qquad (III)$$

(wherein $R^4$ is an alkyl group or halogenated alkyl group having 1 to 10 carbon atoms), or a group represented by the following formula (IV):

$$-OCOR^5 \qquad (IV)$$

(wherein $R^5$ is an alkyl group or halogenated alkyl group having 1 to 10 carbon atoms), and particularly, a halogen atom is preferred. As the examples of $R^4$ and $R^5$, an alkyl group having 1 to 10 carbon atoms such as methyl, ethyl, propyl, butyl groups, etc. and halogenated alkyl group having 1 to 10 carbon atoms such as trifluoromethyl, fluoromethyl, chloromethyl, chloroethyl, chloropropyl groups, etc. are mentioned.

n represents an integer of 2 to 5, and 2 and 3 are particularly preferred.

$R^3$ is an alkyl group having 1 to 10 carbon atoms such as methyl, ethyl, propyl, butyl groups, etc. and particularly methyl and ethyl groups are preferred.

$R^2$ is a hydrogen atom or alkyl group having 1 to 10 carbon atoms such as methyl, ethyl, propyl, butyl groups, etc. and either α-position or β-position is acceptable. Particularly α-methyl and β-methyl groups are preferred.

Specific examples of corticoid 17α-alkoxycarbonyl carbonate derivatives of the present invention include, for example, 4-pregnene-11β,17α,21-triol-3,20-dione 17α-(β-methoxycarbonyl propionate); 4-pregnene-17α,21-diol-3,11,20-trione 17α-(β-methoxycarbonyl propionate); 4-pregnene-11β,17α,21-triol-3,20-dione 17α-(β-methoxycarbonyl propionate)21-propionate; 9α-fluoro-16β-methyl-1,4-pregnadiene-11β,17α,21-triol-3,20-dione 17α-(β-methoxycarbonyl propionate); 9α-fluoro-16α-methyl-1,4-pregnadiene-11β,17α,21-triol-3,20-dione 17α-(β-methoxycarbonyl propionate); 9α-fluoro-16β-methyl-1,4-pregnadiene-11β,17α,21-triol-3,20-dione 17α-(β-methoxycarbonyl propionate)21-propionate; 9α-fluoro-16β-methyl-1,4-pregnadiene-11β,17α,21-triol-3,20-dione 17α-(β-methoxycarbonyl propionate)21-methanesulfonate; 9α-fluoro-16β-methyl-1,4-pregnadiene-11β,17α,21-triol-3,20-dione 17α-(β-ethoxycarbonyl propionate); 21-chloro-9α-fluoro-1,4-pregnadiene-11β,17α-diol-3,20-dione 17α-(β-methoxycarbonyl propionate); 21-chloro-9α-fluoro-16β-methyl-1,4-pregnadiene-11β,17α-diol-3,20-dione 17α-(β-methoxycarbonyl propionate); 21-chloro-9α-fluoro- 16β-methyl-1,4-pregnadiene-11β,17α-diol-3,20-dione 17α-(β-ethoxycarbonyl propionate); 21-chloro-9α-fluoro-16β-methyl-1,4-pregnadiene-11β,17α-diol-3,20-dione 17α-(γ-methoxycarbonyl butylate); 21-chloro-9α-fluoro-16β-methyl-1,4-pregnadiene-11β,17α-diol-3,20-dione 17α-(γ-ethoxycarbonyl butylate); 9α,21-difluoro-16β-methyl-1,4-pregnadiene-11β,17α-diol-3,20-dione 17α-(β-methoxycarbonyl propionate); 21-chloro-9α-fluoro-16α-methyl-1,4-pregnadiene-11β,17α-diol-3,20-dione 17α-(β-methoxycarbonyl propionate); 9α,21-dichloro-16β-methyl-1,4-pregnadiene-11β,17α-diol-3,20-dione 17α-(β-methoxycarbonyl propionate); 21-chloro-9α-fluoro-16β-methyl-1,4-pregnadiene-11β,17α-diol-3,6,20-trione 17α-(β-methoxycarbonyl propionate); 21-chloro-9α-fluoro-16α-methyl-1,4-pregnadiene-11β,17α-diol-3,6,20-trione 17α-(β-methoxycarbonyl propionate); 21-chloro-9α-fluoro-16β-methyl-1,4-pregnadiene-11β,17α-diol-3,6,20-trione 17α-(γ-methoxycarbonyl butyrate); 21-chloro-9α-fluoro-16β-methyl-1,4-pregnadiene-11β,17α-diol-3,6,20-trione 17α-(β-ethoxycarbonyl propionate); 9α-fluoro-16β-methyl-1,4-pregnadiene-11β,17α,21-triol-3,6,20-trione 17α-(β-methoxycarbonyl propionate)21-propionate; 9α-fluoro-16β-methyl-1,4-pregnadiene-11β,17α,21-triol-3,6,20-trione 17α-(β-methoxycarbonyl propionate) 21-methanesulfonate; 9α-fluoro-16β-methyl-1,4-pregnadiene-11β,17α,21-triol-3,6,20-trione 17α-(β-methoxycarbonyl propionate); 9α-chloro-16β-methyl-1,4-pregnadiene-11β,17α,21-triol-3,6,20-trione 17α-(β-methoxcarbonyl propionate); 6α,9α-difluoro-16β-methyl-1,4-pregnadiene-11β,17α,21-triol-3,20-dione 17α-(β-methoxycarbonyl propionate); 9α-fluoro-6α,16β-dimethyl-1,4-pregnadiene-11β,17α,21-triol-3,20-dione 17α-(β-methoxycarbonyl propionate); 9α-fluoro-16β-methyl-1,4-pregnadiene-6β,11β,17α,21-tetraol-3,20-dione 17α-(β-methoxycarbonyl propionate); 6α,21-difluoro-16β-methyl-1,4-pregnadiene-11β,17α-diol-3,6,20-trione 17α-(β-methoxycarbonyl propionate); etc. and 21-position halogenated derivatives such as 21-chloro-9α-fluoro-16β-methyl-1,4-pregnadiene-11β,17α-diol-3,20-dione 17α-(β-methoxycarbonyl propionate); 21-chloro-9α-fluoro-16β-methyl-1,4-pregnadiene-11β,17α-diol-3,20-dione 17α-(β-ethoxycarbonyl propionate); 21-chloro-9α-fluoro-16β-methyl-1,4-pregnadiene-11β,17α-diol-3,20-dione 17α-(γ-methoxycarbonyl butyrate); 21-chloro-9α-fluoro-16β-methyl-1,4-pregnadiene-11β,17α-diol-3,20-dione 17α-(γ-ethoxycarbonyl butyrate); 9α,21-difluoro-16β-methyl-1,4-pregnadiene-11β,17α-diol-3,20-dione 17α-(β-methoxycarbonyl propionate); etc. and 6-oxo, 21-halogenated derivatives such as 21-chloro-9α-fluoro-16β-methyl-1,4-pregnadiene-11β,17α-diol-3,6,20-trione 17α-(β-methoxycarbonyl propionate); 21-chloro-9α-fluoro-16β-methyl-1,4-pregnadiene-11β,17α-diol-3,6,20-trione 17α-(β-ethoxycarbonyl propionate); 21-chloro-9α-fluoro-16β-methyl-1,4-pregnadiene-11β,17α-diol-3,6,20-trione 17α-(γ-methoxycarbonyl butyrate); 21-chloro-9α-fluoro-16β-methyl-1,4-pregnadiene-11β,17α-diol-3,6,20-trione 17α-(γ-ethoxycarbonyl butyrate); 9α-21-difluoro-16β-methyl-1,4-pregnadiene-11β,17α-diol-3,6,20-trione 17α-(β-methoxycarbonyl propionate); etc. are particularly preferred since they have strong local antiphlogistic activity.

Now, the method for producing the compounds of the present invention is set forth below according to the definition of $R^1$ of the general formula (I).

(A) The derivatives of the general formula (I) wherein $R^1$ is a hydroxy group, i.e. 17α-alkoxycarbonyl carboxylate 21-ol derivatives represented by the general formula (Ia):

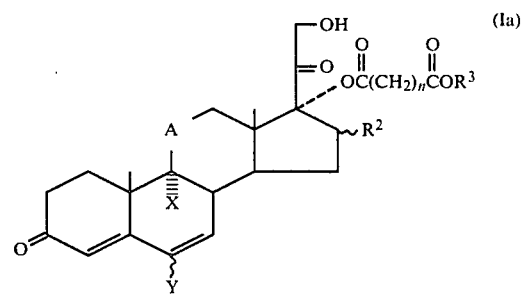

[wherein A, X, Y, $R^2$, n and $R^3$ have the same significance as defined in the general formula (I)].

The derivatives are prepared by reacting a 17α,21-diol substance of the formula (IV) with an orthoester of the formula (V) under acidic conditions to obtain a 17α,21-orthoester derivative of the formula (VI) as shown in the reaction scheme below, and hydrolyzing the 17α,21-orthoester derivative under acidic conditions. The 17α,21-diol substances of the formula (IV) are described in Arzneim. Forsch., 32(I), 317 (1982) and Japanese Unexamined Patent Publication No. 73765/79.

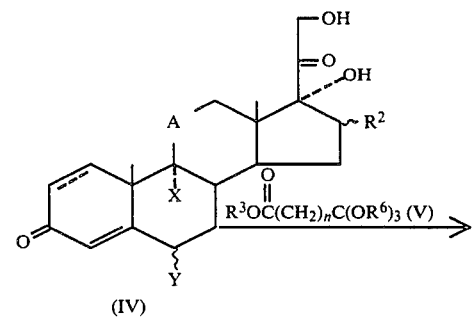

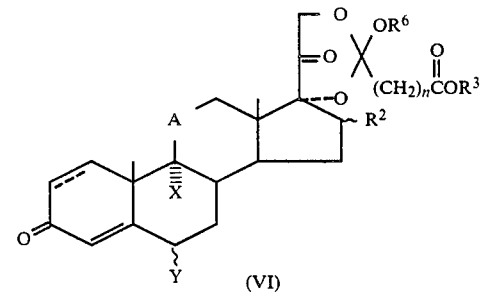

[wherein A, X, Y, $R^2$, $R^3$ and n have the same significance as defined in the general formula (I) and $R^6$ is an alkyl group having 1 to 10 carbon atoms].

As the orthoesters of the formula (V), for example, trimethyl ortho β-methoxycarbonyl propionate, triethyl ortho β-ethoxycarbonyl propionate, trimethyl ortho γ-methoxycarbonyl butyrate, triethyl ortho γ-ethoxycarbonyl butyrate, etc. are mentioned and the amount to be used is 1-3 moles per one mole of 17α,21-diol substance of the formula (IV).

The reaction to obtain 17α,21-orthoester derivatives of the formula (VI) is carried out without any solvent or in a solvent such as benzene, dioxane, tetrahydrofuran, methylene chloride, ethyl acetate, etc. As the acid catalyst, organic sulfonic acids such as p-toluene sulfonic acid, benzene sulfonic acid, etc. as well as pyridine hydrochloride, sulfuric acid, etc. are used. The reaction temperature is $-10°$–$70°$ C. and the reaction period is about 0.5–5 hours.

In the hydrolyzing reaction, organic carboxylic acids such as acetic acid, propionic acid, valeric acid, etc., organic sulfonic acids such as p-toluenesulfonic acid, benzenesulfonic acid, etc. and inorganic acids such as hydrochloric acid, sulfuric acid, etc. are used. However, in this case, 21-alkoxycarbonyl carboxylates are formed as by-products simultaneously with the desired 17α-alkoxycarbonyl carboxylate of the formula (Ia). Therefore, in order to suppress by-production of 21-alkoxycarbonyl carboxylates, it is preferable to maintain the pH of the reaction solution at 5 to 6 by adding metal salts of organic acids such as sodium acetate, potassium propionate, etc. in addition to organic carboxylic acids such as acetic acid, propionic acid, etc., or to employ Lewis acids such as aluminum chloride, zinc chloride, etc. but employment of Lewis acids are more preferable.

Where Lewis acids are used, aqueous alcohols or aqueous cyclic ethers such as aqueous tetrahydrofuran, aqueous dioxane, etc. are used and preferably aqueous alcohols are used. As such alcohols, those represented by the general formula: $R^3OH$ [wherein $R^3$ has the same significance as defined in the general formula (I)] are preferred. Use of other alcohols is undesirable since it is possible to induce transesterification reaction resulting in the contamination of the reaction product. Content of water in the aqueous alcohol is normally 0.5 to 40 weight %. The reaction temperature is 0° to 50° C. and the reaction period is 0.5 to 5 hours.

(B) The derivatives of the general formula (I) wherein $R^1$ is a group $-OSO_2R^4$, i.e. 21-sulfonate derivatives represented by the following general formula (Ib):

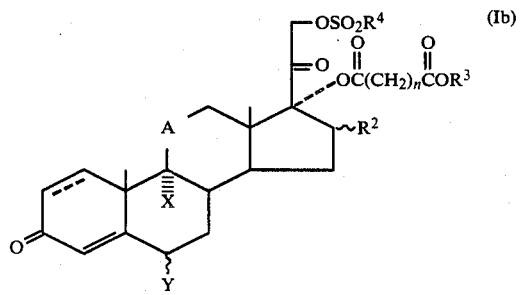

(Ib)

[wherein A, X, Y, $R^2$, n, $R^3$ and $R^4$ have the same significance as defined in the general formulae (I) and (II)].

These derivatives are prepared by reacting 17α-alkoxycarbonyl carboxylate 21-ol derivatives of the formula (Ia) obtained in above (A) with a sulfonic acid anhydride or sulfonic acid halide represented by the general formula (IIa) or (IIb):

[wherein $R^4$ has the same significance as defined in general formula (II) and $X^1$ is a halogen atom].

Such sulfonic acid derivatives include, for example, methanesulfonyl chloride, p-toluenesulfonyl chloride, trifluoromethanesulfonyl chloride, trifluoromethanesulfonic acid anhydride, etc. The amount to be used is 1 to 3 mole per one mol of 17α-alkoxycarbonyl carboxylate 21-ol derivatives of the formula (Ia).

As the solvent, aromatic amines such as pyridine and aliphatic tertiary amines such as triethyl amine are used, which may be diluted with halogenated hydrocarbons such as methylene chloride, dichloroethane, etc.

The reaction temperature is from a room temperature to $-40°$ C. and the reaction period is from 5 minutes to 2 hours.

(C) The derivatives of the general formula (I) wherein $R^1$ is a group $-OCOR^5$, i.e. 21-carboxylate derivatives represented by the general formula (Ic):

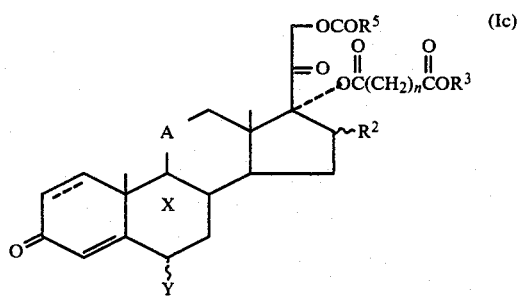

(Ic)

[wherein A, X, Y, n, $R^2$, $R^3$ and $R^5$ have the same significance as defined in the general formulae (I) and (III)].

These derivatives are prepared by reacting 17α-alkoxycarbonyl carboxylate 21-ol derivatives of the formula (Ia) obtained in (A) above with a carboxylic acid anhydride or carboxylic acid halide represented by the general formula (IIIa) or (IIIb):

[wherein $R^5$ has the same significance as defined in the general formula (III) and $X^1$ is a halogen atom].

As the carboxylic acid derivatives, for example, acetic acid anhydride, propionic acid anhydride, butylyl chloride and cyclopropylcarbonyl chloride are mentioned. The amount to be used is 1 to 3 mols per 1 mol of 17α-alkoxycarbonyl carboxylate 21-ol derivatives of the formula (Ia).

As the solvent, aromatic amines such as pyridine, and aliphatic tertiary amines such as triethyl amines are used, which may be diluted with halogenated hydrocarbons such as methylene chloride, dichloroethane, etc.

The reaction temperature is from $-30°$ C. to 50° C. and the reaction period is 5 minutes to 3 hours.

(D) The derivatives of the general formula (2) wherein $R^1$ is a halogen atom, i.e. 21-halogenated corticoid represented by the general formula (Id):

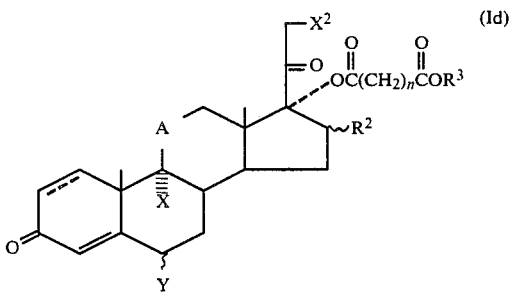

[wherein A, X, Y, n, $R^2$ and $R^3$ have the same significance as defined in the general formula (I) and $X^2$ is a halogen atom].

The compounds are prepared by reacting 21-sulfonate derivatives of the formula (Ib) obtained according to the process described in (B) above with a halogen ion-donor.

As the halogen ion-donor, lithium chloride, lithium bromide, lithium iodide, potassium chloride, etc. are mentioned. The amount of the reagent to be used is 1 to 10 mols per 1 mol of 21-sulfonate derivatives of the formula (Ib).

As examples of 21-sulfonate, methane sulfonate, p-toluene sulfonate and trifluoromethane sulfonate are mentioned.

The reaction is carried out in an aprotic solvent such as dimethylformamide, dimethylacetamide, dimethylsulfoxide, etc. at 0°–120° C. Usually, the reaction period is 0.5–20 hours.

Further, 21-halogenated corticoids represented by general formula (Id)':

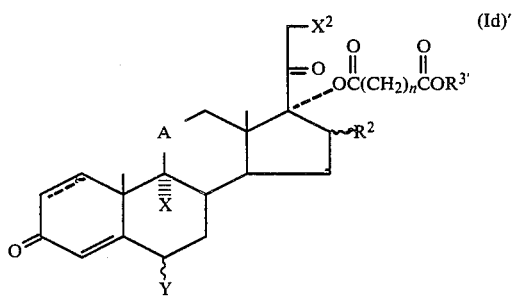

[wherein A, X, Y, n, $X^2$ and $R^2$ have the same significance as defined in the general formulae (Id) and $R^{3\prime}$ is an alkyl group having 1 to 10 carbon atoms, which is different from $R^3$ of the general formula (Id)] are obtained by reacting 21-halogenated corticoids of the formula (Id) with alcohols represented by the general formula: $R^{3\prime}OH$ (VII) [wherein $R^{3\prime}$ has the same significance as defined in the general formula (Id)'] to effect transesterification.

In the above transesterification reaction, inorganic acids such as hydrochloric acid, sulfuric acid, etc., alkali metal hydroxides such as sodium hydroxide and potassium hydroxide and alkali metal compounds of alcohols which correspond to the desired ester, such as sodium methoxide, sodium ethoxide, sodium propoxide, potassium methoxide, etc. are used as catalysts. As the solvent, an excess volume of absolute alcohols such as methanol, ethanol, propanol, etc. which corresponds to the desired ester is used.

The reaction temperature is 0°–60° C. and the reaction period is 1 to 20 hours.

17α-alkoxycarbonyl carboxylate derivatives of the formula (I) obtained in the above (A)–(D) can be purified by recrystallization.

17α-alkoxycarbonyl carboxylate derivatives (I) of the present invention have strong topical anti-inflammatory activity and are weak in systemic side effects. Therefore, they are very useful as anti-inflammatory agent, particularly, as topical anti-inflammatory agent.

The derivatives of the present invention may be formulated into a preparation suitable for topical administration in conventional manner with the aid of one or more carriers or excipients. Examples of types of preparation include ointments, lotions, creams, sprays, powders, drops (e.g., ear drops and eye drops), suppositories or retention enemas (e.g., for the treatment of rectal or colonic inflammations) and tablets or pellets (e.g., for the treatment of aphthous ulcers) and aerosols.

The proportion of active steroid in the compositions according to the invention depends on the precise type of formulations to be prepared but will generally be within the range of from 0.0001% to 5% by weight. Generally, however, for most types of preparations advantageously the proportion used will be within the range of from 0.001 to 0.5% and preferably 0.01 to 0.25%.

Now, the present invention is explained more in detail referring to examples but it can not be limited to the examples so far as it is within the gist thereof.

EXAMPLE 1

4-pregnene-11β,17α,21-triol-3,20-dione
17α-(β-methoxycarbonyl propionate)

To 1.0 g of 4-pregnene-11β,17α,21-triol-3,20-dione are added 15 ml of tetrahydrofuran, 0.02 g of p-toluenesulfonic acid and 1.33 g of trimethyl ortho β-methoxycarbonyl propionate and the mixture is stirred at room temperature for 3 hours.

The resulting reaction mixture is poured into ice water containing sodium bicarbonate and extracted with ethyl acetate. The organic layer is washed with water and dried with magnesium sulfate. After removing the solvent by distillation, 2.2 g of an oily matter is obtained.

The oily matter is dissolved in chloroform and charged in a column packed with 40 g of silica gel. Elution is carried out with benzene-ethyl acetate (4:1) and the solvent is removed by distillation. 0.52 g of 4-pregnene-11β,17α,21-triol-3,20-dione 17α,21-methyl ortho β-methoxycarbonyl propionate are obtained as an amorphous solid.

0.52 g of 4-pregnene-11β,17α,21-triol-3,20-dione 17α,21-methyl ortho β-methoxycarbonyl propionate are dissolved into 20 ml of methanol. To the solution are added 0.8 ml of 0.28% aqueous solution of aluminum monochloride and the mixture is stirred at room temperature for 6 hours. The reaction mixture is poured into 100 ml of saturated saline solution. Extraction is carried out with ethyl acetate followed by washing with water and drying. After the solvent is removed by distillation, the resulting residue is subjected to purification by chromatography using silica gel (benzene:ethyl acetate=3:1). As the result, 0.43 g of 4-pregnene-11β,17α,21-triol-3,20-dione 17α-(β-methoxycarbonyl propionate) are obtained as an amorphous solid.

IR: 3460, 2950, 1735, 1660 cm$^{-1}$

NMR (CDCl$_3$, δ): 0.93 (S, 18-CH$_3$), 1.43 (S, 19-CH$_3$), 2.60 (S, 17-OCOCH$_2$CH$_2$COO—), 4.28 (d, 21—-CH$_2$), 5.70 (S, 4-CH)

EXAMPLE 2

9α-fluoro-16β-methyl-1,4-pregnadiene-11β,17α,21-triol-3,20-dione 17α-(β-methoxycarbonyl propionate)

To 2.0 g of 9α-fluoro-16β-methyl-1,4-pregnadiene-11β,17α,21-triol-3,20-dione are added 21 ml of tetrahydrofuran, 2.5 g of trimethyl ortho β-methoxycarbonyl propionate and 0.03 g of p-toluene sulfonic acid and the mixture is stirred at room temperature for 3 hours and then left standing overnight.

The resulting reaction mixture is poured into ice water containing sodium bicarbonate and extracted with ethyl acetate. After washing with water and drying, the solvent is removed by distillation to give 4.0 g of a residue.

The residue is subjected to purification by column chromatography using silica gel (benzene:ethyl acetate=4:1) and 2.0 g of 9α-fluoro-16β-methyl-1,4-pregnadiene-11β,17α,21-triol-3,20-dione 17α,21-methyl ortho β-methoxycarbonyl propionate are obtained as an amorphous solid.

2.0 g of 9α-fluoro-16β-methyl-1,4-pregnadiene-11β,17α,21-triol-3,20-dione 17α,21-methyl ortho β-methoxycarbonyl propionate are dissolved in 55 ml of methanol and 3.3 ml of 0.28% aqueous solution of aluminum monochloride is added thereto. Reaction is carried out at room temperature for 5 hours and the reaction mixture is left standing overnight. The reaction mixture is then poured into 300 ml of saturated saline solution and extracted with ethyl acetate. After washing with water and drying, the solvent is removed by distillation to give 1.88 g of crystals. The crystals are recrystallized from ethyl acetate-n-hexane. As the result, 1.78 g of 9α-fluoro-16β-methyl-1,4-pregnadiene-11β,17α,21-triol-3,20-dione 17α-(β-methoxycarbonyl propionate) are obtained.

Melting point: 227°-230° C.
IR: 3460, 2950, 1735, 1665 cm$^{-1}$
NMR (DMSO-d$_6$, δ): 0.88 (S, 18-CH$_3$), 1.48 (S, 19-CH$_3$), 2.57 (S, 17-OCOCH$_2$CH$_2$COO—), 3.40 (S, 17-CO$_2$CH$_3$), 5.33 (S, 11β-OH), 6.0 (S, 4-CH), 6.2 (d-d, 2-CH), 7.27 (d, 1-CH)

EXAMPLE 3

9α-fluoro-16β-methyl-1,4-pregnadiene-11β,17α,21-triol-3,6,20-trione 17α-(β-methoxycarbonyl propionate)

To 6.51 g of 9α-fluoro-16β-methyl-1,4-pregnadiene-11β,17α,21-triol-3,6,20-trione are added 61 ml of tetrahydrofuran, 9.23 g of trimethyl ortho β-methoxycarbonyl propionate and 0.11 g of p-toluene sulfonic acid. Reaction is carried out at room temperature for 5 hours and then the reaction mixture is left standing overnight.

The reaction mixture is poured into ice water containing sodium bicarbonate and extracted with ethyl acetate. After washing with water and drying, the solvent is removed by distillation to give 15.7 g of a residue.

After purification by chromatography using silica gel (benzene:ethyl acetate=4:1), 5.79 g of crystals of 9α-fluoro-16β-methyl-1,4-pregnadiene-11β,17α,21-triol-3,6,20-trione 17α,21-methyl ortho β-methoxycarbonyl propionate are obtained (Melting point: 180°-185° C.).

5.70 g of 9α-fluoro-16β-methyl-1,4-pregnadiene-11β,17α,21-triol-3,6,20-trione 17α,21-methyl ortho β-methoxycarbonyl propionate are dissolved in 180 ml of methanol and 60 ml of ethyl acetate, and 8.6 ml of 0.28% aqueous solution of aluminum chloride are added thereto. Reaction is carried out at room temperature for 5 hours and the reaction mixture is left standing overnight. The reaction mixture is then poured into 600 ml of saturated saline solution and extracted with ethyl acetate. After washing with water and drying, the solvent is removed by distillation. As the result, 5.41 g of 9α-fluoro-16β-methyl-1,4-pregnadiene-11β,17α,21-triol-3,6,20-trione 17α-(β-methoxycarbonyl propionate are obtained as crystals.

Melting point: 175°-179° C.
IR: 3460, 2950, 1735, 1705, 1663 cm$^{-1}$
NMR (CDCl$_3$, δ): 0.98 (S, 18-CH$_3$), 1.50 (S, 19-CH$_3$), 2.62 (S, 17-OCOCH$_2$CH$_2$COO—), 6.35 (S, 4-CH)

EXAMPLE 4

21-chloro-9α-fluoro-16β-methyl-1,4-pregnadiene-11β,17α-diol-3,20-dione 17α-(β-methoxycarbonyl propionate)

To 690 mg of 9α-fluoro-16β-methyl-1,4-pregnadiene-11β,17α,21-triol-3,20-dione 17α-(β-methoxycarbonyl propionate) obtained in Example 2 are added 10 ml of methylene chloride and 0.51 ml of triethylamine and further 0.51 ml of methanesulfonyl chloride is added thereto under ice cooling. After 10 minutes, the reaction mixture is restored to room temperature, and stirred for 30 minutes. Thereafter, 30 ml of methylene chloride are added to the reaction mixture, which is washed successively with 1N-hydrochloric acid, saturated aqueous solution of sodium hydrogen carbonate and saturated saline solution and dried.

After removing the solvent by distillation, 729 mg of 9α-fluoro-16β-methyl-1,4-pregnadiene-11β,17α,21-triol-3,20-dione 17α-(β-methoxycarbonyl propionate)21-methanesulfonate are obtained as an amorphous solid.

To 729 mg of 9α-fluoro-16β-methyl-1,4-pregnadiene-11β,17α,21-triol-3,20-dione 17α-(β-methoxycarbonyl propionate)21-methanesulfonate are added 8 ml of dimethylformamide and 404 mg of lithium chloride, and the mixture is stirred at 80° C. for 11 hours.

Dimethylformamide is removed by distillation under reduced pressure and methylene chloride is added to the residue. The mixture is thoroughly washed with water and dried. After the solvent is removed by filtration, 651 mg of an oily matter are obtained. Purification is carried out by column chromatography using silica gel and 547 mg 21-chloro-9α-fluoro-16β-methyl-1,4-pregnadiene-11β,17α-diol-3,20-dione 17α-(β-methoxycarbonyl propionate) are obtained as crystals. Recrystallization is carried out from ethyl acetate-n-hexane.

Melting point: 215°-216° C.
Elementary analysis: Found (%): C, 61.98; H, 6.50. Calcd. (%) for C$_{27}$H$_{34}$O$_7$ClF: C, 61.77; H, 6.53.
IR: 3460, 3000, 1745, 1680 cm$^{-1}$
NMR (DMSO-d$_6$, δ): 0.88 (S, 18-CH$_3$), 1.50 (S, 19-CH$_3$), 2,61 (S, 17-OCOCH$_2$CH$_2$COO—), 3.55 (S, 17-COOCH$_3$), 4.71 (S, 21-CH$_2$), 6.0 (S, 4-CH), 6.22 (d-d, 2-CH), 7.27 (d, 1-CH)

EXAMPLE 5

21-chloro-9α-fluoro-16β-methyl-1,4-pregnadiene-11β,17α-diol-3,6,20-trione 17α-(β-methoxycarbonyl propionate)

To 5.31 g of 9α-fluoro-16β-methyl-1,4-pregnadiene-11β,17α,21-triol-3,6,20-trione 17α-(β-methoxycarbonyl propionate) obtained in Example 3 are added 105 ml of methylene chloride and 3.86 mg of triethylamine and 1.03 ml of methanesulfonyl chloride are further added thereto under ice cooling. After ten minutes, the reaction mixture is restored to room temperature and stirred for 50 minutes. Then, the reaction mixture is washed with 1N-hydrochloric acid, saturated aqueous solution of sodium hydrogen carbonate and saturated saline solution and dried.

After removing the solvent by distillation, 6.31 g of 9α-fluoro-16β-methyl-1,4-pregnadiene-11β,17α,21-triol-3,6,20-trione 17α-(β-methoxycarbonyl propionate)21-methane sulfonate are obtained as an amorphous solid.

To 6.31 g of 9α-fluoro-16β-methyl-1,4-pregnadiene-11β,17α,21-triol-3,6,20-trione 17α-(β-methoxycarbonyl propionate) 21-methane sulfonate are added 45 ml of dimethylformamide and 3.03 g of lithium chloride and the mixture is stirred at 80° C. for 15 hours.

Dimethylformamide is removed by distillation under reduced pressure and methylene chloride is added to a residue. After thoroughly washing with water and drying, the solvent is removed by distillation to give 5.7 g of a residue.

Purification is carried out by chromatography using silica gel (benzene:ethyl acetate=4:1) and 3.83 g of 21-chloro-9α-fluoro-16β-methyl-1,4-pregnadiene-11β,17α-diol-3,6,20-trione 17α-(β-methoxycarbonyl propionate) are obtained as crystals. Recrystallization is carried out from ethyl acetate-n-hexane.

Melting point: 183°–187° C.
IR: 3460, 2950, 1735, 1705, 1660 cm$^{-1}$
NMR (CDCl$_3$, δ): 1.03 (S, 18-CH$_3$), 1.57 (S, 19-CH$_3$), 2.65 (S, 17-OCOCH$_3$), 4.07 (S, 21-CH$_2$), 6.50 (S, 4-CH)

EXAMPLE 6

21-chloro-9α-fluoro-16α-methyl-1,4-pregnadiene-11β,17α-diol-3,20-dione 17α-(β-methoxycarbonyl propionate)

To 2.0 g of 9α-fluoro-16α-methyl-1,4-pregnadiene-11β,17α,21-triol-3,20-dione are added 20 ml of tetrahydrofuran, 2.45 g of trimethyl ortho β-methoxycarbonyl propionate and 0.03 g of p-toluene sulfonic acid. Reaction is carried out at room temperature for 5 hours and the reaction mixture is left standing overnight.

The reaction mixture is poured to ice water containing sodium bicarbonate and extracted with ethyl acetate. After washing with water and drying, the solvent is removed by distillation. The resulting residue is purified by chromatography using silica gel (benzene:ethyl acetate=4:(1) and 1.71 g of 9α-fluoro-16α-methyl-1,4-pregnadiene-11β,17α,21-triol-3,20-dione 17α,21-methyl ortho β-methoxycarbonyl propionate are obtained as crystals.

To 1.71 g of 9α-fluoro-16α-methyl-1,4-pregnadiene-11β,17α,21-triol-3,20-dione 17α,21-methyl orthomethoxycarbonyl propionate are added 80 ml of methanol, 20 ml of ethyl acetate and 4 ml of 0.28% aqueous solution of aluminum monochloride and the mixture is stirred at 40° C. for 2 hours. The reaction mixture is poured into saturated saline solution and extracted with ethyl acetate. After washing with water and drying, the solvent is removed by distillation to give 1.70 g of crude crystals of 9α-fluoro-16α-methyl-1,4-pregnadiene-11β,17α,21-triol-3,20-dione 17α-(β-methoxycarbonyl propionate).

To 1.70 g of 9α-fluoro-16α-methyl-1,4-pregnadiene-11β,17α,21-triol-3,20-dione 17α-(β-methoxycarbonyl propionate) are added 25 ml of methylene chloride and 1.27 ml of triethylamine, and 0.34 ml of methanesulfonyl chloride are further added thereto under ice-cooling. After 10 minutes, the mixture is restored to room temperature and stirred for 30 minutes.

25 ml of methylene chloride is added to the reaction mixture and the resulting mixture is washed with 1N-hydrochloric acid, saturated aqueous solution of sodium hydrogen carbonate and saturated saline solution and then dried. After removing the solvent by distillation, 1.89 g of 9α-fluoro-16α-methyl-1,4-pregnadiene-11β,17α,21-triol-3,20-dione 17α-(β-methoxycarbonyl propionate)21-methanesulfonate are obtained as an amorphous solid.

To 1.89 g of 9α-fluoro-16α-methyl-1,4-pregnadiene-11β,17α,21-triol-3,20-dione 17α-(β-methoxycarbonyl propionate)21-methanesulfonate are added 1.0 g of lithium chloride and 30 ml of dimethylformamide and the mixture is stirred at 80° C. for 20 hours.

The solvent is removed by distillation under reduced pressure and methylene chloride is added thereto. The mixture is thoroughly washed with water and dried. Then, methylene chloride is removed by distillation and the residue is purified by chromatography using silica gel (benzene:ethyl acetate=4:1). As the result, 1.11 g of crystals of 21-chloro-9α-fluoro-16α-methyl-1,4-pregnadiene-11β,17α-diol-3,20-dione 17α-(β-methoxycarbonyl propionate) are obtained.

Melting point: 210°–214° C.
IR: 3460, 2960, 1740, 1670 cm$^{-1}$
NMR (CDCl$_3$, δ): 1.07 (S, 18-CH$_3$), 1.55 (S, 19-CH$_3$), 2.62 (S, 17-OCOCH$_2$CH$_2$COO—), 3.65 (S, 17-COOCH$_3$), 4.03 (S, 21-CH$_2$), 6.10 (S, 4-CH), 6.27 (d-d, 2-CH)

EXAMPLE 7

21-chloro-9α-fluoro-16β-methyl-1,4-pregnadiene-11β,17α-diol-3,20-dione 17α-(γ-ethoxycarbonyl butyrate)

To 2.0 g of 9α-fluoro-16β-methyl-1,4-pregnadiene-11β,17α,21-triol-3,20-dione are added 35 ml of tetrahydrofuran, 2.0 g of triethyl ortho γ-ethoxycarbonyl butyrate and 40 mg of p-toluenesulfonic acid and the mixture is stirred at room temperature for 7 hours and then left standing overnight.

The reaction mixture is poured into ice water containing sodium bicarbonate and extracted with ethyl acetate. After washing with water and drying, the solvent is removed by distillation and the residue is purified by chromatography using silica gel (benzene:ethyl acetate=4:1). As the result, 0.90 g of crystals of 9α-fluoro-16β-methyl-1,4-pregnadiene-11β,17α,21-triol-3,20-dione 17α,21-ethyl ortho γ-ethoxycarbonyl butyrate are obtained (Melting point: 150°–155° C.).

To 0.90 g of 9α-fluoro-16β-methyl-1,4-pregnadiene-11β,17α,21-triol-3,20-dione 17α,21-ethyl ortho γ-ethoxycarbonyl butyrate are added 30 ml of ethanol and 1.35 ml of 0.28% aqueous solution of aluminum chloride, and reaction is carried out at room temperature for 4 hours.

The reaction mixture is poured into saturated saline solution and extracted with ethyl acetate. After washing with water and drying, the solvent is removed by distillation to give 0.77 g of 9α-fluoro-16β-methyl-1,4-pregnadiene-11β,17α,21-triol-3,20-dione 17α-(γ-ethoxycarbonyl butyrate) as an amorphous solid.

To 0.60 g of 9α-fluoro-16β-methyl-1,4-pregnadiene-11β,17α,21-triol-3,20-dione 17α-(γ-ethoxycarbonyl butyrate) are added 12 ml of methylene chloride and 0.42 ml of triethylamine, and 0.11 ml of methanesulfonyl chloride are further added thereto under ice-cooling. After 10 minutes, the mixture is restored to room temperature and further stirred for 3 hours.

The reaction mixture is washed with 1N-hydrochloric acid, saturated aqueous solution of sodium hydrogen carbonate and saturated saline solution. After drying, the solvent is removed by distillation and 0.71 g of 9α-fluoro-16β-methyl-1,4-pregnadiene-11β,17α,21-triol-3,20-dione 17α-(γ-ethoxycarbonyl butyrate)21-methane sulfonate are obtained as an amorphous solid.

To 0.71 g of 9α-fluoro-16β-methyl-1,4-pregnadiene-11β,17α,21-triol-3,20-dione 17α-(γ-ethoxycarbonyl butyrate)21-methane sulfonate are added 5 ml of dimethylformamide and 0.33 g of lithium chloride, and the mixture is stirred at 80° C. for 12 hours.

After the solvent is removed by distillation under reduced pressure, methylene chloride is added to the residue and the mixture is thoroughly washed with water and dried. The solvent is removed by distillation and the residue is purified by chromatography using silica gel (benzene:ethyl acetate=4:1). As the result, 0.55 g of 21-chloro-9α-fluoro-16β-methyl-1,4-pregnadiene-11β,17α-diol-3,20-dione 17α-(γ-ethoxycarbonyl butyrate) are obtained as an amorphous solid.

IR: 3450, 2950, 1735, 1665 cm$^{-1}$

NMR (CDCl$_3$, δ): 1.02 (S, 18-CH$_3$), 1.57 (S, 19-CH$_3$), 1.23 and 4.10 (t and q, 17-OCOCH$_2$CH$_3$), 4.00 (S, 21-CH$_2$), 6.12 (S, 4-CH), 6.28 (d-d, 2-CH)

EXAMPLE 8

9α-fluoro-16β-methyl-1,4-pregnadiene-11β,17α,21-triol-3,20-dione 17α-(β-methoxycarbonyl propionate)21-propionate To 0.80 g of 9α-fluoro-16β-methyl-1,4-pregnadiene-11β,17α,21-triol-3,20-dione 17α-(β-methoxycarbonyl propionate) obtained in Example 2 are added 8 ml of methylene chloride and 0.60 ml of triethyl amine, and 0.2 ml of propionyl chloride are further added thereto under ice-cooling. After 10 minutes, the mixture is restored to room temperature and stirred for further two hours.

50 ml of methylene chloride is added to the reaction mixture and the resulting mixture is washed with 1N-hydrochloric acid, saturated aqueous solution of sodium hydrogen carbonate and saturated saline solution and dried. The solvent is removed by distillation and the residue is purified by chromatography using silica gel (benzene:ethyl acetate=4:1). As the result, 0.57 g of 9α-fluoro-16β-methyl-1,4-pregnadiene-11β,17α,21-triol-3,20-dione 17α-(β-methoxycarbonyl propionate)21-propionate are obtained as an amorphous solid.

IR: 3470, 2960, 1740, 1670 cm$^{-1}$

NMR (CDCl$_3$, δ): 1.00 (S, 18-CH$_3$), 1.55 (S, 19-CH$_3$), 2.62 (S, 17-OCOCH$_2$CH$_2$COO—), 3.65 (S, 17-COOCH$_3$), 6.12 (S, 4-CH), 6.32 (d-d, 2-CH)

EXAMPLE 9

21-chloro-9α-fluoro-16β-methyl-1,4-pregnadiene-11β,17α-diol-3,20-dione 17α-(β-ethoxycarbonyl propionate)

To 500 mg of 21-chloro-9α-fluoro-16β-methyl-1,4-pregnadiene-11β,17α-diol-3,20-dione 17α-(β-methoxycarbonyl propionate) obtained in Example 4 is added a solution of 4.4 mg of metallic sodium in 10 ml of ethanol and the mixture is stirred at room temperature for 2.5 hours and then left standing overnight.

The reaction mixture is poured into saturated saline solution and extracted with ethyl acetate. After washing with water and drying, the solvent is removed by distillation and the residue is purified by chromatography using silica gel (benzene:ethyl acetate=4:1). As the result, 360 mg of crystals of 21-chloro-9α-fluoro-16β-methyl-1,4-pregnadiene-11β,17α-diol-3,20-dione 17α-(β-ethoxycarbonyl propionate) are obtained. The crystals are recrystallized from ethyl acetate-n-hexane.

Melting point: 228°–230° C.

IR: 3460, 2950, 1740, 1670 cm$^{-1}$

NMR (CDCl$_3$, δ): 1.30 (S, 18-CH$_3$), 1.58 (S, 19-CH$_3$), 1.22 and 4.08 (t and q, 17-COOCH$_2$CH$_3$), 6.07 (S, 4-CH), 6.27 (d-d, 2-CH)

EXPERIMENTAL EXAMPLE

[Method]

Experiments are conducted, according to the following procedures, on topical anti-inflammatory activity and on thymolytic action which is an index of systemic side effects, for the purpose of clarifying pharmacological activities of the compounds of the present invention.

(1) Experiment on topical anti-inflammatory activity

Male mice of ddY-strain having a body weight of 15–20 g are divided at random into groups, each consisting of 10 mice.

0.9% sodium chloride, 0.4% Tween 80, 0.5% carboxymethyl cellulose and 0.9% benzyl alcohol are dissolved or suspended in distilled water, which is used as a suspending medium.

The compounds to be tested are dissolved in a mixture of the suspending medium:pyridine:diethyl ether=1:4:5 and mixed with equal volume of diethyl ether containing 10% croton oil and the mixture is used as the test liquid.

Commercially available felt having a thickness of 5 mm is cut in 7 mm×7 mm square and adhered to ring tweezers using alkyl-α-cyanoacrylate. The felt is soaked in the test liquid and the liquid is applied to the right ear of the mouse by rubbing it with the felt at a fixed pressure without anesthesia. The left ear is left untreated. At 5th hours after application, mice are killed and both of the ears are cut and weighed. The rate (%) of increase in the weight of right ear against that of left ear is calculated as the edema ratio. Edema ratios obtained on the test compounds are compared with those obtained on control and edema-repressing rate is obtained.

(2) Experiment on thymolytic action

Male rats of Wistar strain having a body weight of 120–150 g are divided at random into groups, each consisting of 8 rats.

The compounds to be tested are dissolved in a liquid consisting of croton oil:cotton seed oil:ethanol=1:89:10 and the solution is used for injection.

The rats are anesthesized by inhalation of ether and 20 ml of air are subcutaneously injected at the back of the rats using a thin injection needle to form an oval-shaped air cavity. After the rats recovered from anesthesia, they are kept on normal food and water. At 8th days after injection, rats are killed by depletion and dissected. The thymus gland is taken out and the wet weight is measured. Thymus weights obtained on the test compounds are devided with those obtained on control, and thymus gland atrophy rate is obtained.

[Results]

In each of the experiments on anti-inflammatory activity and thymolytic action, clobetasol 17-propionate and betamethasone 17,21-dipropionate are used as standard compounds and anti-inflammatory activity ratio and thymolytic activity ratio against clobetasol 17-propionate are calculated using linear regression parallel test method.

The results are shown in Table 1 below. In the Table, the compounds are indicated by relevant Example numbers.

TABLE 1

| Compounds | Anti-inflammatory activity ratio (A) | Thymolytic activity ratio (B) | R = A/B |
|---|---|---|---|
| Clobetasol 17-propionate | 1 | 1 | 1 |
| Example 4 | 1.3 | 0.072 | 18 |
| Example 5 | 1.0 | <0.01 | >100 |
| Example 6 | 0.2 | <0.01 | >20 |
| Example 7 | 0.68 | 0.012 | 57 |
| Example 9 | 0.56 | 0.007 | 80 |
| Betamethasone 17,21-dipropionate | 0.080 | 0.030 | 2.7 |

As is apparent from the above Table 1, the compounds of the present invention show an anti-inflammatory activity comparable to or better than that of clobetasol 17-propionate.

With respect to thymolytic action, all the compounds of the present invention have weaker action than clobetasol 17-propionate.

Thus, since the present compounds have very weak systemic side effects and strong topical anti-inflammatory activity, it is obvious that they are useful compounds.

What is claimed is:

1. A corticoid compound of the formula (I):

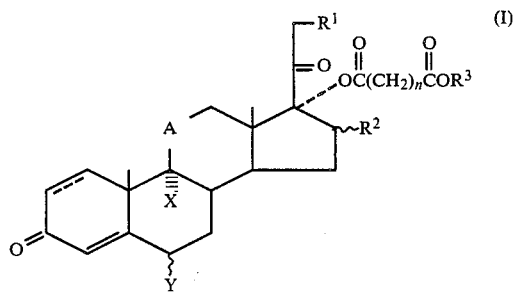

wherein A is a group

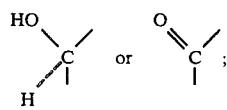

X is a hydrogen atom or halogen atom; Y is a hydrogen atom, oxo group, α- or β-halogen atom, hydroxyl group or alkyl group having 1 to 10 carbon atoms; n is an integer of 2 to 5; $R^1$ is a hydroxyl group, halogen atom, a group represented by the formula (II):

 (II)

wherein $R^4$ is an alkyl group or halogenated alkyl group having 1 to 10 carbon atoms, or a group represented by the formula (III):

—OCOR⁵, (III)

wherein $R^5$ is an alkyl group or halogenated alkyl group having 1 to 10 carbon atoms, $R^2$ is a hydrogen atom or alkyl group having 1 to 10 carbon atoms at the α- or β-position, and the bond between $C_1$ and $C_2$ is a single bond or double bond.

2. 4-Pregnene-11β,17α,21-triol-3,20-dione 17α(β-methoxycarbonyl propionate).

3. 9α-Fluoro-16β-methyl-1,4-pregnadiene-11β,17α,21-triol-3,20-dione 17α-(β-methoxycarbonyl propionate).

4. 9α-Fluoro-16β-methyl-1,4-pregnadiene-11β,17α,21-triol-3,6,20-trione 17α-(β-methoxycarbonyl propionate).

5. 21-Chloro-9α-fluoro-16β-methyl-1,4-pregnadiene-11β,17α-diol-3,20-dione 17α-(β-methoxycarbonyl propionate).

6. 21-Chloro-9α-fluoro-16β-methyl-1,4-pregnadiene-11β,17α-diol-3,6,20-trione 17α-(β-methoxycarbonyl propionate).

7. 21-Chloro-9α-fluoro-16α-methyl-1,4-pregnadiene-11β,17α-diol-3,6,20-dione 17α-(β-methoxycarbonyl propionate).

8. 21-Chloro-9α-fluoro-16β-methyl-1,4-pregnadiene-11β,17α-diol-3,20-dione 17α-(γ-ethoxycarbonyl butyrate).

9. 9α-Fluoro-16β-methyl-1,4-pregnadiene-11β,17α,21-triol-3,20-dione 17α-(β-methoxycarbonyl propionate)21-propionate.

10. 21-Chloro-9α-fluoro-16β-methyl-1,4-pregnadiene-11β,17α-diol-3,20-dione 17α-(β-ethoxycarbonyl propionate).

11. Process for producing a corticoid 17α,21-orthoester derivative of the formula (VI):

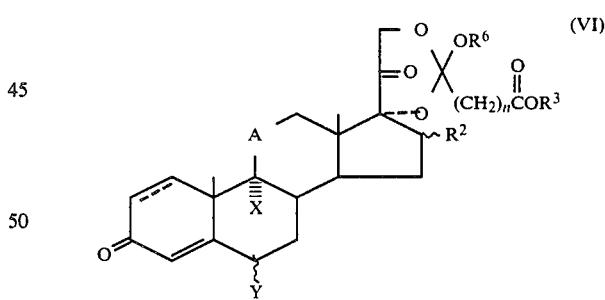

wherein A is a group

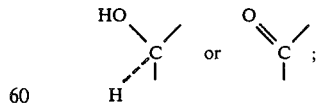

X is a hydrogen atom or halogen atom; Y is a hydrogen atom, oxo group, α- or β-halogen atom, hydroxyl group or alkyl group having 1 to 10 carbon atoms; $R^2$ is a hydrogen atom or alkyl group having 1 to 10 carbon atoms at the α- or β-position; n is an integer of 2 to 5; $R^3$ and $R^6$ are alkyl groups having 1 to 10 carbon atoms; and the bond between $C_1$ and $C_2$ is a single bond or double bond, characterized by reacting a compound represented by the formula (IV):

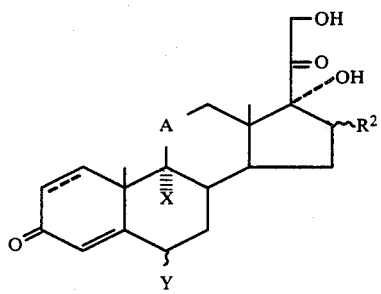

wherein A, X, Y and $R^2$ have the same significance as defined in the general formula (VI) with an orthoester represented by the formula (V):

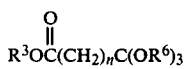

wherein n, $R^3$ and $R^6$ have the same significance as defined in the formula (VI).

12. Process for producing a corticoid 17α-alkoxycarbonyl carboxylate derivative of the formula (Id):

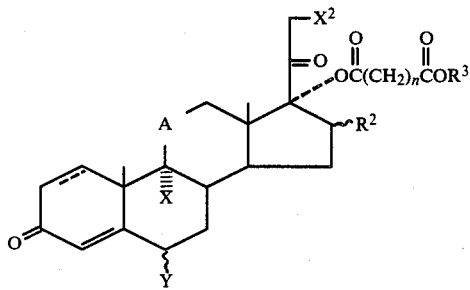

wherein A is a group

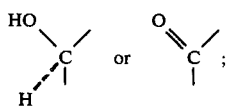

X is a hydrogen atom or halogen atom; Y is a hydrogen atom, oxo group, α- or β-halogen atom, hydroxyl group or alkyl group having 1 to 10 carbon atoms; $R^2$ is a hydrogen atom or alkyl group having 1 to 10 carbon atoms at the α- or β-position; n is an integer of 2 to 5; $R^3$ is an alkyl group having 1 to 10 carbon atoms; $X^2$ is a halogen atom; and the bond between $C_1$ and $C_2$ is a single bond or double bond, characterized by reacting a compound represented by the formula (Ib):

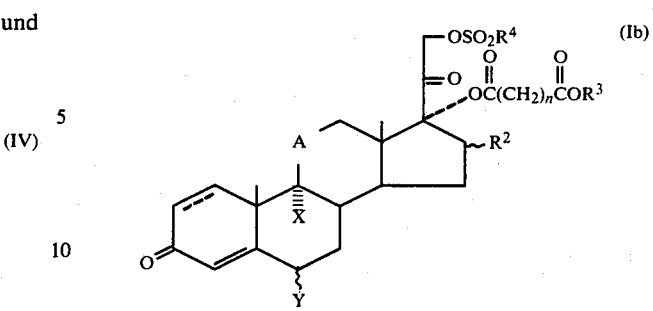

wherein A, X, Y, $R^2$, n and $R^3$ have the same significance as defined in the formula (Id) and $R^4$ is an alkyl group or halogenated alkyl group having 1 to 10 carbon atoms with a halogen ion-releasing reagent.

13. Process for producing a corticoid 17α-alkoxycarbonyl carboxylate derivative of the formula (Id)':

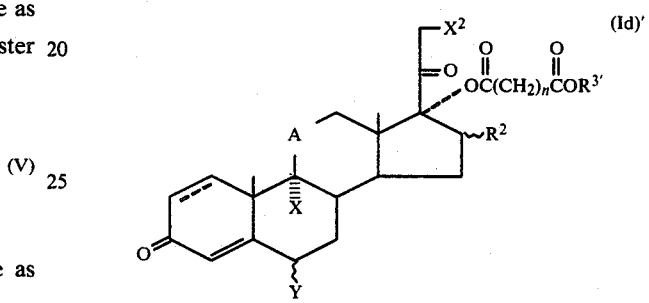

wherein A is a group

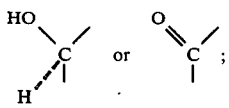

X is a hydrogen atom or halogen atom; Y is a hydrogen atom, oxo group, α- or β-halogen atom, hydroxy group or alkyl group having 1 to 10 carbon atoms; $R^2$ is a hydrogen atom or alkyl group having 1 to 10 carbon atoms at the α- or β-position; $X^2$ is a halogen atom; n is an integer of 2 to 5; $R^{3'}$ is an alkyl group having 1 to 10 carbon atoms; and the bond between $C_1$ and $C_2$ is a single bond or double bond), characterized by reacting a compound represented by the following formula (Id):

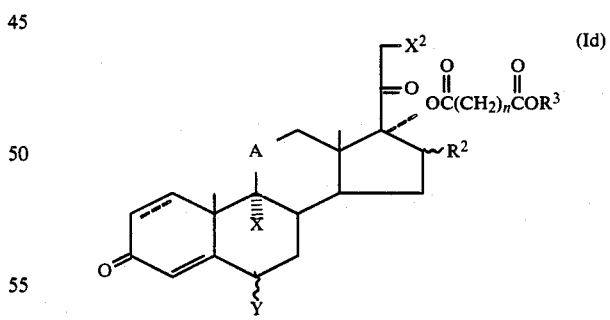

wherein A, X, Y, $R^2$, $X^2$ and n have the same significance as defined in the formula (Id)' and $R^3$ is an alkyl group having 1 to 10 carbon atoms but is different from $R^{3'}$ of the general formula (Id)' with an alcohol represented by the formula (VII):

$R^{3'}$—OH  (VII)

wherein $R^{3'}$ has the same significance as defined in the general formula (Id)' to effect interesterification.

14. A pharmaceutical composition consisting of a pharmaceutically effective amount of the derivatives represented by the formula (I) and a pharmaceutically acceptable carrier.

* * * * *